(12) United States Patent
Takezaki et al.

(10) Patent No.: US 11,376,628 B2
(45) Date of Patent: Jul. 5, 2022

(54) CAPACITIVE DEVICE AND PIEZOELECTRIC DEVICE

(71) Applicant: Hitachi, Ltd., Tokyo (JP)

(72) Inventors: Taiichi Takezaki, Tokyo (JP); Hiroaki Hasegawa, Tokyo (JP); Shuntaro Machida, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 383 days.

(21) Appl. No.: 16/534,012

(22) Filed: Aug. 7, 2019

(65) Prior Publication Data

US 2020/0070205 A1 Mar. 5, 2020

(30) Foreign Application Priority Data

Sep. 5, 2018 (JP) .............................. JP2018-165730

(51) Int. Cl.
*B06B 1/02* (2006.01)
*G01N 29/24* (2006.01)
*A61B 8/00* (2006.01)
*B06B 1/06* (2006.01)

(52) U.S. Cl.
CPC .......... *B06B 1/0292* (2013.01); *A61B 8/4494* (2013.01); *B06B 1/067* (2013.01); *G01N 29/245* (2013.01); *G01N 29/2406* (2013.01); *A61B 8/4483* (2013.01)

(58) Field of Classification Search
CPC .... B06B 1/0292; B06B 1/067; G01N 29/245; G01N 29/2406; G01N 29/0672; H02N 1/006; A61B 8/4494
See application file for complete search history.

(56) References Cited

U.S. PATENT DOCUMENTS

| | | | | |
|---|---|---|---|---|
| 6,004,832 A | * | 12/1999 | Haller | ................... B06B 1/0292 |
| | | | | 216/2 |
| 2007/0013269 A1 | * | 1/2007 | Huang | .................. B81B 3/0021 |
| | | | | 310/334 |
| 2007/0164632 A1 | | 7/2007 | Adachi et al. | |
| 2010/0013574 A1 | * | 1/2010 | Huang | .................. B06B 1/0292 |
| | | | | 333/186 |

(Continued)

FOREIGN PATENT DOCUMENTS

JP 2001-145192 A 5/2001
JP 2009-55474 A 3/2009

(Continued)

OTHER PUBLICATIONS

Japanese-language Office Action issued in Japanese Application No. 2018-165730 dated Sep. 28, 2021 with English translation (seven (7) pages).

(Continued)

*Primary Examiner* — Helen C Kwok
(74) *Attorney, Agent, or Firm* — Crowell & Moring LLP

(57) ABSTRACT

A capacitive device includes a unit cell including a CMUT, and a transmission/reception plate for impedance matching which is provided above the unit cell via a connection portion, in which a membrane of the CMUT constituting the unit cell is connected to the transmission/reception plate via the connection portion having an area smaller than that of the transmission/reception plate. The area of the transmission/reception plate is desirably larger than the area of a hollow portion of the CMUT.

3 Claims, 5 Drawing Sheets

(56) References Cited

U.S. PATENT DOCUMENTS

| | | | |
|---|---|---|---|
| 2010/0020991 A1 | 1/2010 | Chen | |
| 2010/0232257 A1* | 9/2010 | Tanaka | G01N 29/0672 367/7 |
| 2015/0163599 A1* | 6/2015 | Shim | B06B 1/0292 381/150 |
| 2015/0230029 A1* | 8/2015 | Hong | B06B 1/0685 381/396 |
| 2016/0020709 A1* | 1/2016 | Shim | B06B 1/0292 310/300 |

FOREIGN PATENT DOCUMENTS

| | | |
|---|---|---|
| JP | 2009-194934 A | 8/2009 |
| JP | 2013-146478 A | 8/2013 |

OTHER PUBLICATIONS

Japanese-language Office Action issued in Japanese Application No. 2018-165730 dated Apr. 12, 2022 with English translation (eight (8) pages).

* cited by examiner

CAPACITIVE DEVICE AND PIEZOELECTRIC DEVICE

BACKGROUND OF THE INVENTION

1. Field of the Invention

The present invention relates to a capacitive device and a piezoelectric device, and more particularly to a capacitive device and a piezoelectric device which include a transmission/reception plate for impedance matching.

2. Description of the Related Art

An ultrasonic transducer element is incorporated in an ultrasonic probe (probe) of an ultrasonic imaging apparatus, transmitting and receiving ultrasonic waves and used for various purposes, such as diagnosis of a tumor in a human body or non-destructive inspection for cracks generated in a building.

Conventionally, for this type of probes of ultrasonic imaging apparatuses, piezoelectric ceramics represented by lead zirconate titanate (PZT) or the like has been used as an electro-acoustic transducer element, but in recent years, capacitive micromachined ultrasonic transducers (hereinafter abbreviated as CMUTs) having wider bandwidth characteristics than that of the piezoelectric ceramics have attracted attention and studied and developed (JP 2013-146478 A, JP 2009-194934A, and JP 2009-055474 A).

The CMUT is basically structured so that a hollow portion (cavity) is defined in an insulating layer between a lower electrode and an upper electrode arranged above the lower electrode, and the insulating layer and the upper electrode which are positioned above the hollow portion are functioned as a membrane (also referred to as diaphragm). For transmission of ultrasonic waves, direct voltage and alternating voltage are superimposed and applied between the upper electrode and the lower electrode to vibrate the membrane at the frequency of the alternating voltage by an electrostatic force generated between both electrodes at that time. On the other hand, for reception of ultrasonic waves, the pressure of the ultrasonic waves reaching a surface of the membrane vibrates the membrane, and a change in distance between both electrodes generated at that time is electrically detected as a change in capacitance.

SUMMARY OF THE INVENTION

In non-destructive inspection using ultrasonic waves, in order to improve ultrasonic wave propagation efficiency, objects to be inspected are often immersed in water for the inspection.

However, the states of many of the objects to be inspected changes due to swelling in water or water penetration, and thus, the objects to be inspected need to be inspected in the air.

However, the sound propagation efficiency of ultrasonic waves propagating in the air to a reception element is as low as 0.001%, which is an obstacle of high-precision inspection in the air.

The above and other objects and novel characteristics of the present invention will be apparent from the description of the present specification and the accompanying drawings.

The following is a brief description of the outline of a typical embodiment disclosed in the present application.

A capacitive device according to the typical embodiment includes a CMUT, a connection portion formed on a membrane of the CMUT and having a first area, and a transmission/reception plate formed above the CMUT via the connection portion and having a second area larger than the first area.

According to the present invention, it is possible to achieve a capacitive device having improved sound propagation efficiency in the air.

DESCRIPTION OF THE PREFERRED EMBODIMENTS

Figure 1:
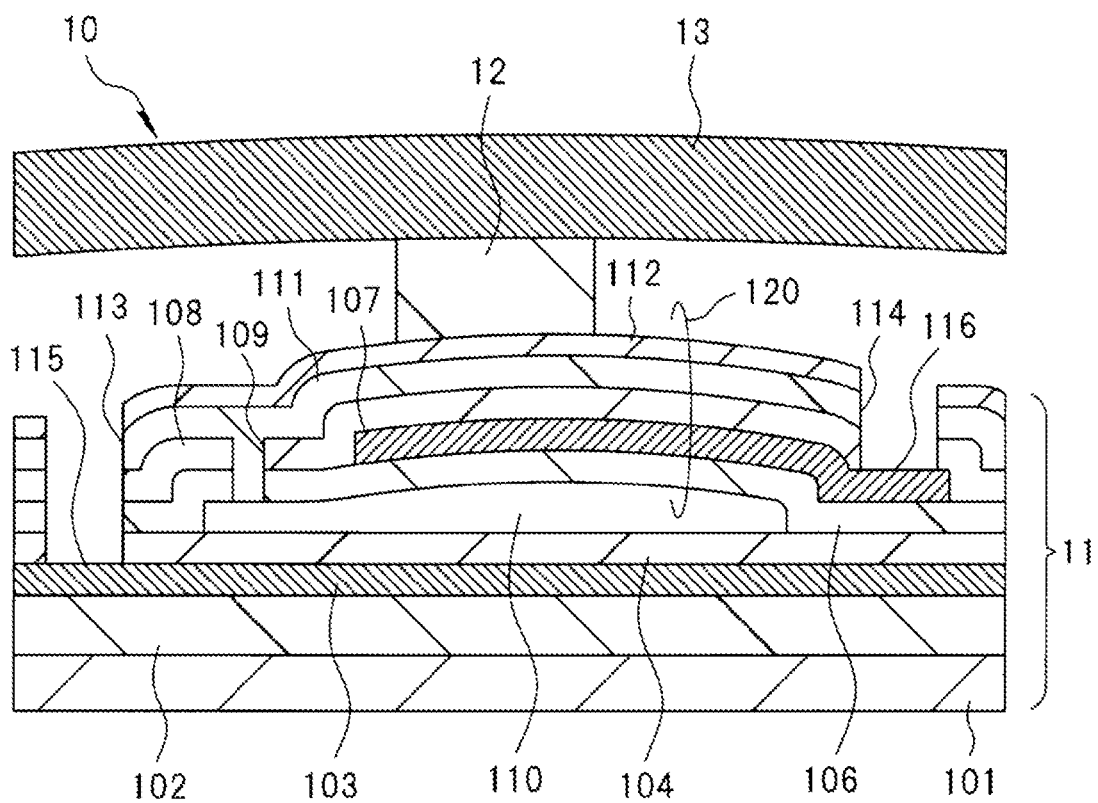
FIG. 1 is a cross-sectional view of a unit structure of a capacitive device according to a first embodiment.

Hereinafter, embodiments of the present invention will be described in detail with reference to the drawings. Note that, in all the drawings for the description of the embodiments, members having the same functions are denoted by the same reference numerals, and the repetitive description thereof will be omitted. In the drawings for the description of the embodiments, hatching may be omitted even in a cross-sectional view, for easy understanding of the configuration.

First Embodiment

FIG. 1 is a cross-sectional view of a unit structure of a capacitive device 10 according to a first embodiment. The capacitive device 10 includes a unit cell 11 including a CMUT (ultrasonic transducer), and a transmission/reception plate 13 for impedance matching which is provided above the unit cell 11 via a connection portion 12.

The unit cell (CMUT) 11 includes a lower electrode 103 formed on a substrate 101 including monocrystalline silicon via an insulating film 102, two layers of insulating films 104 and 106 formed above the lower electrode 103, a hollow portion 110 defined by a gap formed between the two layers of the insulating films 104 and 106, an upper electrode 107 formed above the hollow portion 110 via the insulating film 106, and three layers of insulating films 108, 111, and 112 formed above the upper electrode 107. The insulating films 104, 106, 108, 111, and 112 include a silicon dioxide film.

Here, the insulating films 106, 108, 111, and 112 and the upper electrode 107 have a portion positioned above the hollow portion 110, and the portion functions as a membrane 120 which vibrates when transmitting and receiving ultrasonic waves. Furthermore, the insulating films 106, 108, 111, and 112 has a portion surrounding the region functioning as the membrane 120, and the portion functions as a fixing portion supporting the membrane 120.

The insulating films 104, 106, 108, 111, and 112 each have an opening to define a connection hole 113, and the connection hole 113 has a bottom portion to expose therefrom a pad 115 for external connection constituted by a part of the lower electrode 103, and the insulating films 108, 111 and 112 each have an opening to define a connection hole 114, and the connection hole 114 has a bottom portion to expose therefrom a pad 116 for external connection constituted by a part of the upper electrode 107. To the unit cell 11, direct voltage and alternating voltage are applied from an external power supply through conductor layers (not illustrated) connected to the pads 115 and 116.

The lower electrode 103 is formed by depositing a metal film, such as an aluminum alloy film, over the insulating film 102. The upper electrode 107 is formed by depositing a metal film, such as an aluminum alloy film, over the insulating film 106 and then patterning the metal film by using photolithography and dry etching.

The hollow portion 110 is formed by forming a dummy pattern (not illustrated) made of a polycrystalline silicon film or metal film, over the insulating film 104 and then bringing a wet etching solution into contact with the surface of the dummy pattern through an opening 109 defined in the insulating films 106 and 108 to dissolve the dummy pattern. The hollow portion 110 has, for example, a rectangular planar shape but may have a circular, elliptical, or polygonal planar shape.

The connection portion 12 positioned on the unit cell 11 includes, for example, an insulating film (for example, silicon nitride film) having an etching selectivity to the wet etching solution different from that of the insulating film 112, and the insulating film 112 is formed by depositing this insulating film and a thin film constituting the transmission/reception plate 13 on the insulating film 112 and performing patterning by using a difference in etching rate between this insulating film and the insulating film 112.

The transmission/reception plate 13 provided above the unit cell 11 via the connection portion 12 may be a conductive film including, for example, an aluminum alloy or an insulating film, but a material having a low density and a high Young's modulus is preferably employed. The transmission/reception plate 13 has, for example, a rectangular planar shape but may have a circular, elliptical, or polygonal planar shape.

In addition, the materials of the electrodes and insulating films which constitute the unit cell 11 described above are only a preferable example, the materials are not limited to the above description, and various materials used for semiconductor manufacturing processes can be used. In other words, for the lower electrode 103, the upper electrode 107, and the transmission/reception plate 13, a metal material other than the aluminum alloy, such as W, Ti, TiN, Al, Cr, Pt, or Au, polycrystalline silicon, amorphous silicon, or the like heavily doped with an impurity can also be used. Furthermore, instead of the insulating film including a silicon dioxide film, a silicon oxynitride film, a hafnium oxide film, a hafnium oxide film with silicon doped, or the like can be used.

The capacitive device 10 according to the present first embodiment is characterized in that the membrane 120 of the CMUT constituting the unit cell 11 is connected to the transmission/reception plate 13 via the connection portion 12 having an area smaller than that of the transmission/reception plate 13. Although it is required that the transmission/reception plate 13 should have an area larger than the area of the connection portion 12, the area of the transmission/reception plate 13 is desirably larger than the area of the hollow portion 110, from the viewpoint of improvement in sound propagation efficiency.

Here, when the impedance of air is $Z_1$ (=00044 Mrayls) and the impedance of the unit cell 11 including the CMUT is $Z_2$ (a general CMUT=approximately several Mrayls), the acoustic reflectance ($R_p$) of sound propagating in the air and reflected on a surface of the capacitive device 10 is expressed by $R_p=(Z_2-Z_1)/(Z_1+Z_2)$. In other words, the reflectance ($R_p$) decreases as $Z_2-Z_1$ decreases (in other words, as $Z_1$ is closer to $Z_2$).

Therefore, the capacitive device 10 according to the present embodiment is provided with the transmission/reception plate 13 having a larger area than that of the connection portion 12 above the unit cell 11 via the connection portion 12, the capacitive device 10 has a larger apparent density of air, increasing the impedance $Z_1$ (=density×speed) of air, reducing the reflectance ($R_p$) relative to that of a transmission/reception element configured by CMUT (unit cell 11) alone, and thus the capacitive device 10 functions as a transmission/reception element having higher sound propagation efficiency.

The capacitive device 10 actually has a composite structure in which a large number of unit structures each including a unit cell 11, a connection portion 12, and a transmission/reception plate 13 as described above are arranged in one direction or two orthogonal directions of a main surface of the substrate 101.

Figure 2:
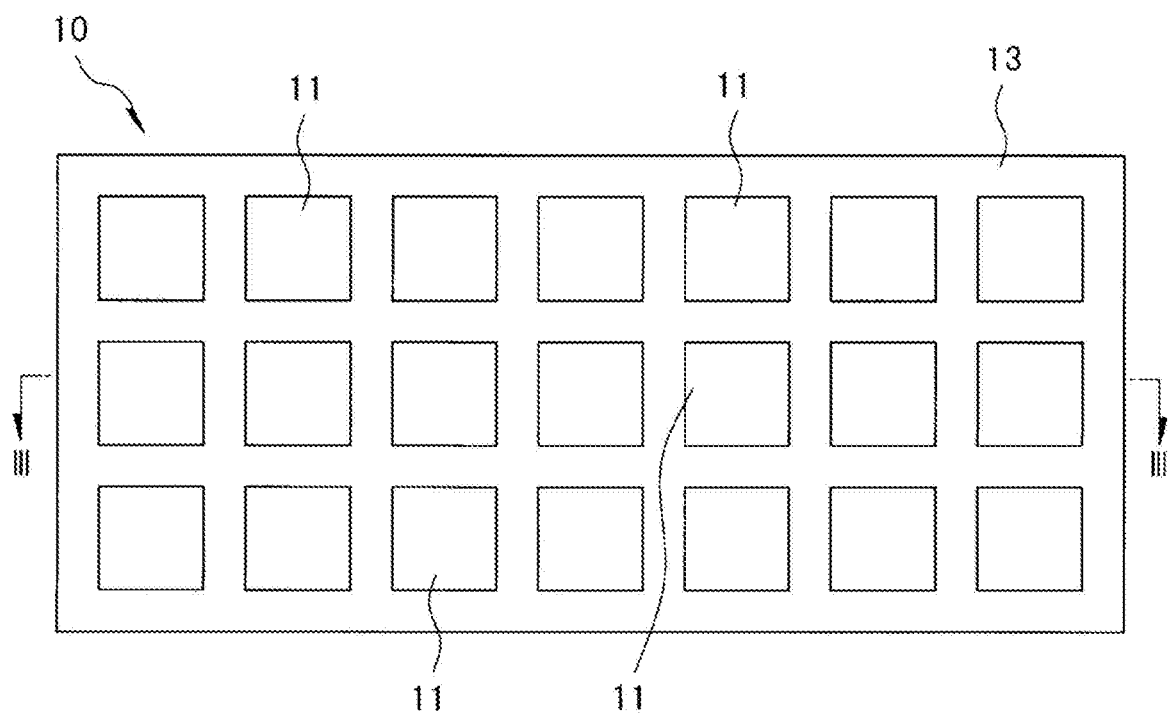
FIG. 2 is a plan view of an example of a capacitive device having a composite structure in which unit cells of the capacitive device according to the first embodiment are arranged in an array.
Figure 3:
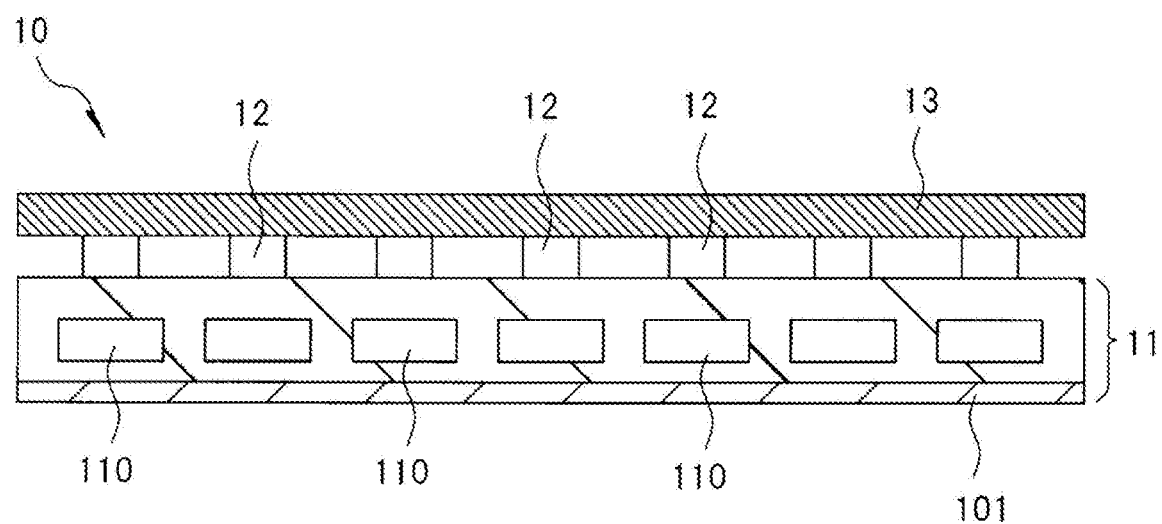
FIG. 3 is a cross-sectional view taken along the line III-III in FIG. 2.

For example, in a capacitive device 10 having a composite structure illustrated in FIG. 2 and FIG. 3 (FIG. 3 is a cross-sectional view taken along the line III-III of FIG. 2), a large number of unit cells 11 are formed on a common substrate 101 into an array, one sheet of the transmission/reception plate 13 is provided above the large number of unit cells 11, and each unit cell 11 is connected to the transmission/reception plate 13 by a connection portion 12 having an area smaller than that of the unit cell 11.

Figure 4:
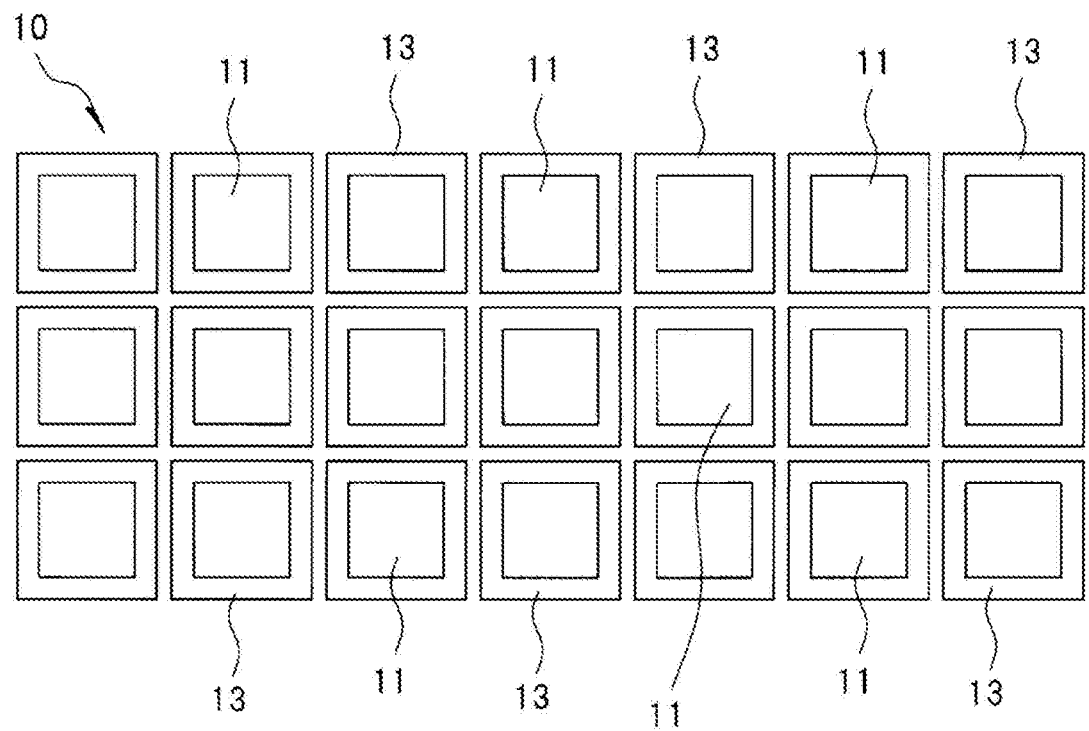
FIG. 4 is a plan view of another example of a capacitive device having a composite structure in which unit cells of FIG. 1 are arranged in an array.

Furthermore, as illustrated in FIG. 4, a capacitive device 10 can adopt a composite structure in which the unit structures illustrated in FIG. 1 are arranged in an array at predetermined intervals. In this case, the array is advantageously formed readily as compared with the composite structure illustrated in FIGS. 2 and 3. Furthermore, since the transmission/reception plate 13 is reduced in size as compared with the composite structure illustrated in FIGS. 2 and 3, suppression of transverse waves and design of frequency are advantageously facilitated.

Second Embodiment

Figure 5:
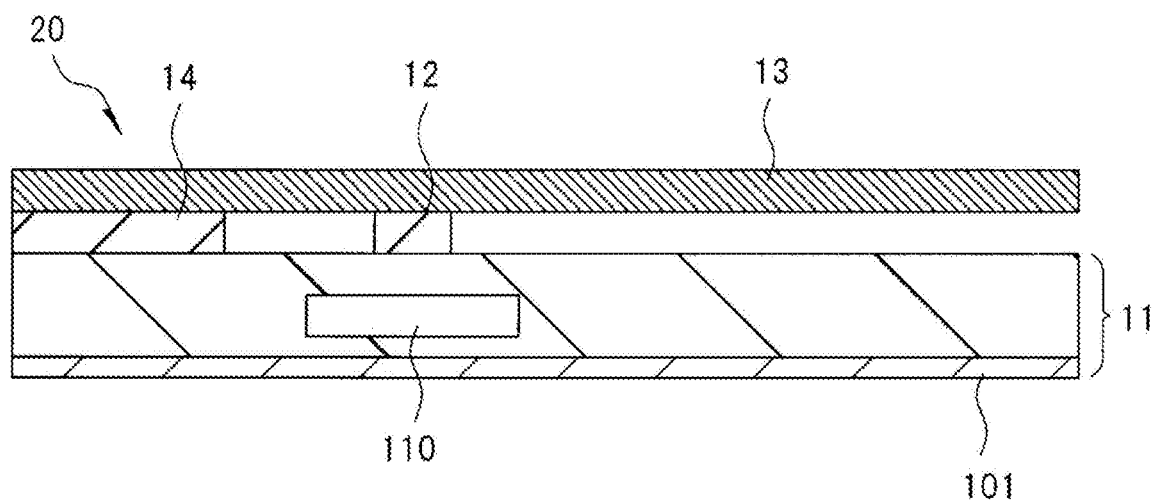
FIG. 5 is a schematic cross-sectional view of a unit structure of a capacitive device according to a second embodiment.

FIG. 5 is a schematic cross-sectional view of a unit structure of a capacitive device 20 according to a second embodiment. The capacitive device 20 according to the second embodiment is characterized in that one end of a transmission/reception plate 13 is supported by a unit cell 11 via a fixing portion 14 including an insulating film positioned in the same layer as a connection portion 12. Furthermore, a hollow portion 110 and a membrane 120 (see FIG. 1) above the hollow portion 110, both of which function as a CMUT, and the connection portion 12 are arranged at a position closer to the fixing portion 14 than the center portion of the transmission/reception plate 13. In other words, the hollow portion 110, the membrane 120, and the connection portion 12 are arranged at a position on a side closer to the fixing portion 14 (left side in FIG. 5) which is less likely to be deformed compared with the other end (right end in FIG. 5) of the transmission/reception plate 13.

The capacitive device 20 according to the present embodiment configured as described above reduces the displacement of the transmission/reception plate 13 upon receiving a sound wave, and thus highly sensitive reception is enabled compared with the capacitive device 10 according to the first embodiment.

Furthermore, as in the unit structure of the capacitive device 10 according to the first embodiment, in the unit structure of the capacitive device 20 according to the second embodiment, the membrane 120 of the CMUT constituting the unit cell 11 is connected to the transmission/reception plate 13 via the connection portion 12 having a smaller area than that of the transmission/reception plate 13, and thus the capacitive device 20 functions as a transmission/reception element having higher sound propagation efficiency.

Figure 6:
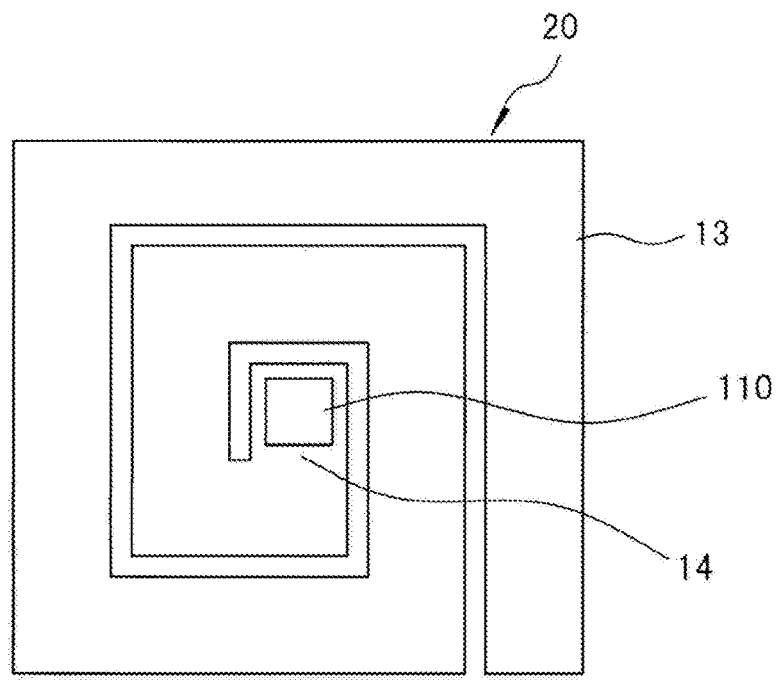
FIG. 6 is a plan view of an example of a planar structure of a transmission/reception plate in a capacitive device according to the second embodiment.

The transmission/reception plate 13 has but is not limited to, for example, a rectangular planar shape, and in a case where the transmission/reception plate 13 has a planar spiral shape as illustrated in FIG. 6, the transmission/reception plate 13 having a larger area than that of the unit cell 11 can be achieved.

Furthermore, as in the case of the capacitive device 10 according to the first embodiment, the capacitive device 20 actually has a composite structure in which a large number of the fixing portions 14 and the above-mentioned unit structures each including the unit cell 11, the connection portion 12, and the transmission/reception plate 13 are arranged in one direction or two orthogonal directions of a main surface of a substrate 101.

Figure 7:
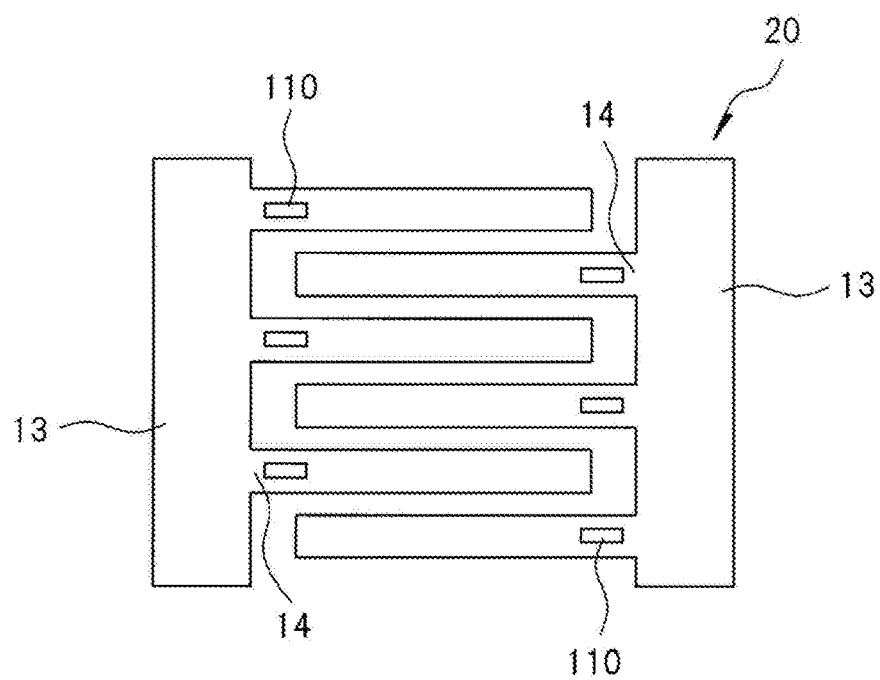
FIG. 7 is a plan view of another example of a planar structure of a transmission/reception plate in a capacitive device according to the second embodiment.
Figure 8:
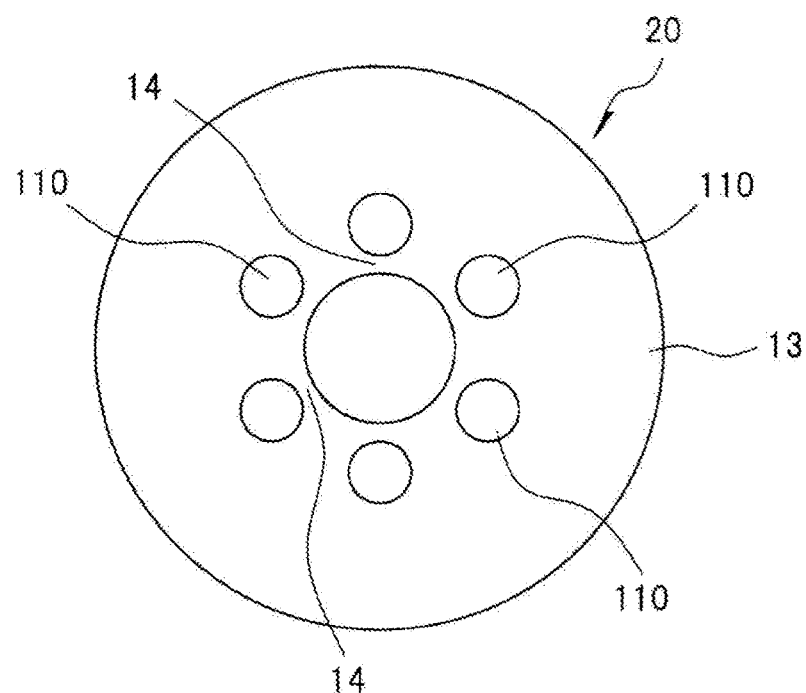
FIG. 8 is a plan view of further another example of a planar structure of a transmission/reception plate in a capacitive device according to the second embodiment.
Figure 9:
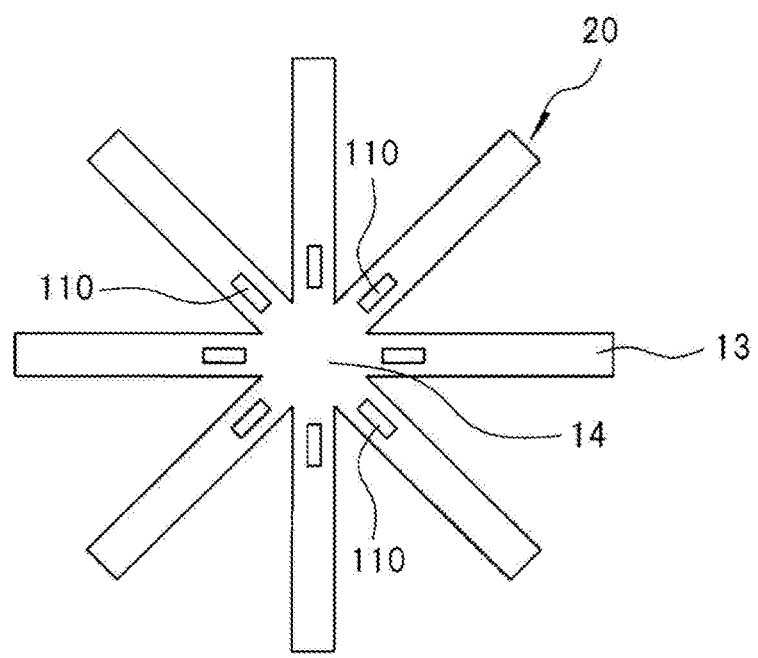
FIG. 9 is a plan view of another example of a planar structure of a transmission/reception plate in a capacitive device according to the second embodiment.

In this case as well, various modifications can be made, for example, a plurality of transmission/reception plates 13 is arranged in a comb-like shape as illustrated in FIG. 7, one sheet of the transmission/reception plate 13 is arranged in an annular shape as illustrated in FIG. 8, and a plurality of transmission/reception plates 13 is arranged radially around a common fixing portion 14 as illustrated in FIG. 9.

As described above, the invention made by the present inventors has been described in detail on the basis of the embodiments, but the present invention is not limited to the above-mentioned embodiments, and various modifications and alterations may be made without departing from the spirit and scope of the invention.

In the capacitive device 10 according to the first embodiment and the capacitive device 20 according to the second embodiment, the transmission/reception plate 13 is provided above the unit cell 11 including the CMUT, via the connection portion 12, but the transmission/reception plate may be provided above a transmission/reception element other than the CMUT, such as a piezoelectric element, via the connection portion.

Although the piezoelectric element has lower sound propagation efficiency than that of the CMUT, in a case where the transmission/reception plate is provided above the piezoelectric element via the connection portion, the sound propagation efficiency can be improved as compared with using only the piezoelectric element.

What is claimed is:

1. A capacitive device comprising:
   an ultrasonic transducer comprising:
      a substrate,
      a lower electrode formed above the substrate,
      a hollow portion provided above a first insulating film and below a second insulating film sequentially formed above the lower electrode,
      an upper electrode formed above the hollow portion,
      a third insulating film formed above the upper electrode, and
      a membrane constituted by the second insulating film and the third insulating film above the hollow portion;
   a connection portion formed on the membrane and having a first area; and
   a transmission/reception plate formed above the ultrasonic transducer via the connection portion and having a second area larger than the first area, wherein
      the second area of the transmission/reception plate is larger than an area of the hollow portion,
      the transmission/reception plate is fixed to the ultrasonic transducer via a fixed portion,
      the transmission/reception plate has a planar spiral shape, and
      the hollow portion, the membrane, and the connection portion are arranged at a position closer to the fixing portion than a center portion of the transmission/reception plate.

2. The capacitive device according to claim 1, wherein a plurality of the ultrasonic transducer arranged in an array is connected to the transmission/reception plate formed above the plurality of the ultrasonic transducer, via a plurality of the connection portion each having an area smaller than an area of the transmission/reception plate.

3. The capacitive device according to claim 1, wherein each of the plurality of the ultrasonic transducer arranged in an array is connected to the transmission/reception plate formed above each of the plurality of the ultrasonic transducer, via the connection portion having an area smaller than an area of the transmission/reception plate.

* * * * *